United States Patent [19]

Xu et al.

[11] Patent Number: 5,801,281
[45] Date of Patent: Sep. 1, 1998

[54] PROCESS FOR PREPARING 1,1'- (1,4-PHENYLENEBIS (METHLENE)-BIS 1,4,8,11-TETRAAZACYCLOTETRADECANE

[75] Inventors: David Xu, Whippany; Prasad Kapa, Parsippany; Oljan Repic, Randolph; Thomas J. Blacklock, Clark, all of N.J.

[73] Assignee: Johnson Matthey PLC, London, England

[21] Appl. No.: 968,086

[22] Filed: Nov. 12, 1997

Related U.S. Application Data

[62] Division of Ser. No. 777,072, Dec. 30, 1996, which is a division of Ser. No. 413,582, Mar. 30, 1995, Pat. No. 5,612,478.

[51] Int. Cl.$^6$ .................... C07C 303/00; C07C 233/00
[52] U.S. Cl. .................... 564/82; 564/90; 564/153; 564/160
[58] Field of Search .................... 564/153, 160, 564/82, 90

[56] References Cited

U.S. PATENT DOCUMENTS

| | | | |
|---|---|---|---|
| 5,021,409 | 6/1991 | Murrer et al. | 514/183 |
| 5,047,527 | 9/1991 | Handel et al. | 540/474 |
| 5,247,075 | 9/1993 | Parker et al. | 540/465 |
| 5,326,861 | 7/1994 | Madison et al. | 540/474 |
| 5,612,478 | 3/1997 | Xu et al. | 540/474 |

FOREIGN PATENT DOCUMENTS

| | | |
|---|---|---|
| 374929 | 6/1990 | European Pat. Off. . |
| 0 389 359 | 9/1990 | European Pat. Off. . |
| WO 93/12096 | 6/1993 | WIPO . |

OTHER PUBLICATIONS

Bridger et al, Journal of Medical Chemistry,38(2):366–378 (Jan. 20, 1995).

Chemical Abstracts, vol. 107, No. 18, Abstract No. 167695 (Nov. 2, 1987).

Brandes et al, Bulletin de la Societe Chimique de France, 133(1):65–73 (1996).

Xu et al., "An Expeditious Synthesis of a Biscyclam . . . ", Tetrahedron Letters, vol. 37, No. 30 (Jul. 22, 1996), pp. 5301–5304.

Ciampolini et al., "Dinickel and Dicopper Complexes . . . ", Inorganic Chemistry, vol. 26, No. 21 (1987), pp. 3527–3533.

*Primary Examiner*—Mukund J. Shah
*Assistant Examiner*—Tamthom T. Ngo
*Attorney, Agent, or Firm*—Pillsbury Madison & Sutro LLP

[57] ABSTRACT

An improved process for preparing 1,1'-[1,4-phenylenebis-(methylene)]-bis-1,4,8,11-tetraazacyclotetradecane comprising the selective functionalization of an acyclic tetraamine, and subsequent dimerization and hydrolyzation/tosylation to obtain a 1,4-phenylenebis-methylene bridged hexatosyl acyclic precursor in a first step, the cyclization of said precursor to obtain a hexatosyl cyclam dimer in a second step, and the detosylation of said cyclam dimer in a third step followed by basification to obtain the desired 1,1'-[1,4-phenylenebis-(methylene)]-bis-1,4,8,11-tetraazacyclotetradecane.

3 Claims, No Drawings

PROCESS FOR PREPARING 1,1'- (1,4-PHENYLENEBIS (METHLENE)-BIS 1,4,8,11-TETRAAZACYCLOTETRADECANE

This is a division of application Ser. No. 08/777,072, filed Dec. 30, 1996, which is a division of U.S. application Ser. No. 08/413,582, filed Mar. 30, 1995, now U.S. Pat. No. 5,612,478.

BACKGROUND OF THE INVENTION

1. Field of the Invention

The present invention relates to the area of cyclam dimers and, more particularly, relates to an improved process for preparing a specific pharmaceutically active 1,4-phenylene-bis-(methylene)-linked cyclam dimer.

2. Description of the Prior Art

U.S. Pat. No. 5,021,409 is directed to a method of treating retroviral infections comprising administering to a mammal in need of such treatment a therapeutically effective amount of a bicyclic macrocyclic polyamine compound. Although the usefulness of certain alkylene and arylene bridged cyclam dimers is generically embraced by the teachings of the reference, no arylene bridged cyclam dimers are specifically disclosed.

WO 93/12096 discloses the usefulness of certain linked cyclic polyamines in combating HIV and pharmaceutical compositions useful therefor. Among the specifically disclosed compounds is 1,1'-[1,4-phenylenebis-(methylene)]-bis-1,4,8,11 tetraazacyclotetradecane (and its acid addition salts), which compound is a highly potent inhibitor of several strains of human immune deficiency virus type 1 (HIV-1) and type 2 (HIV-2).

European Patent Appln. 374,929 discloses a process for preparing mono-N-alkylated polyazamacrocycles comprising reacting the unprotected macrocycle with an electrophile in a non-polar, relatively aprotic solvent in the absence of base. Although it is indicated that the monosubstituted macrocycle is formed preferentially, there is no specific disclosure which indicates that linked bicyclams can be synthesized by this process.

U.S. Pat. No. 5,047,527 is directed to a process for preparing a monofunctionalized (e.g., monoalkylated)cyclic tetramine comprising: 1) reacting the unprotected macrocycle with chrominum hexacarbonyl to obtain a triprotected tetraazacyloalkane compound; 2) reacting the free amine group of the triprotected compound prepared in 1) with an organic (e.g., alkyl) halide to obtain a triprotected monofunctionalized (e.g., monoalkylated) tetraazacycloalkane compound; and 3) de-protecting the compound prepared in 2) by simple air oxidation at acid pH to obtain the desired compound. In addition, the reference discloses alternative methods of triprotection employing boron and phosphorous derivatives and the preparation of linked compounds, including the cyclam dimer 1,1'-[1,4-phenylenebis-(methylene)]-bis-1,4,8,11-tetraazacyclotetradecane, by reacting triprotected cyclam prepared as set forth in 1) above with an organic dihalide in a molar ratio of 2:1, and deprotecting the resultant compound to obtain the desired cyclam dimer.

J. Med. Chem., Vol. 38, No. 2, pgs. 366–378 (1995) is directed to the synthesis and anti-HIV activity of a series of novel phenylenebis(methylene)-linked bis-tetraazamacrocyclic analogs, including the known cyclam dimer 1,1'-[1,4-phenylenebis-(methylene)]-bis-1,4,8,11-tetraazacyclotetradecane. The cyclam dimers disclosed in this reference, including the afore-mentioned cyclam dimer, are prepared by: 1) forming the tritosylate of the tetraazamacrocycle; 2) reacting the protected tetraazamacrocycle with an organic dihalide, e.g., dibromo-p-xylene, in acetonitrile in the presence of a base such as potassium carbonate; and 3) de-protecting the bis-tetraazamacrocycle prepared in 2) employing freshly prepared sodium amalgam, concentrated sulfuric acid or an acetic acid/hydrobromic acid mixture to obtain the desired cyclam dimer, or an acid addition salt thereof.

Although the processes disclosed in U.S. Pat. No. 5,047,527 and the J. Med. Chem. reference are suitable to prepare the cyclam dimer 1,1'-[1,4-phenylene bis-(methylene)]-bis-1,4,8,11-tetraazacyclotetradecane, they involve the use of cyclam as a starting material, a compound which is expensive and not readily available. Accordingly, in view of its potent anti-HIV activity, a number of research endeavors have been undertaken in an attempt to develop a more practical process for preparing 1,1'-[1,4-phenylenebis-(methylene)]-bis-1,4,8,11-tetraazacyclotetradecane.

SUMMARY OF THE INVENTION

The present invention relates to a more efficient and economic process for preparing 1,1'-[1,4-phenylenebis-(methylene)]-bis-1,4,8,11-tetraazacyclotetradecane employing an inexpensive and readily available acyclic tetraamine compound as the starting material. More particularly, the present invention involves the selective functionalization of an acyclic tetraamine, and subsequent dimerization and hydrolyzation/tosylation to obtain a 1,4-phenylenebis-methylene bridged hexatosyl acyclic precursor in a first step, the cyclization of said precursor to obtain a hexatosyl cyclam dimer in a second step, and the detosylation of said cyclam dimer in a third step followed by basification to obtain the desired 1,1'-[1,4-phenylenebis-(methylene)]-bis-1,4,8,11-tetraazacyclotetradecane.

DETAILED DESCRIPTION OF THE INVENTION

The present invention relates to an improved process for preparing 1,1'-[1,4-phenylenebis-(methylene)]-bis-1,4,8,11-tetraazacyclotetradecane by a three-step process as depicted below:

STEP 1

Part 1

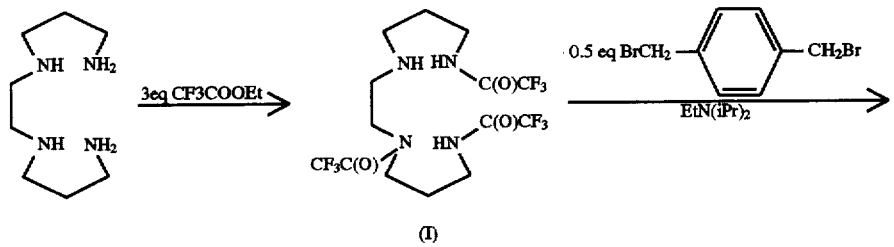

Part 2

Part 3

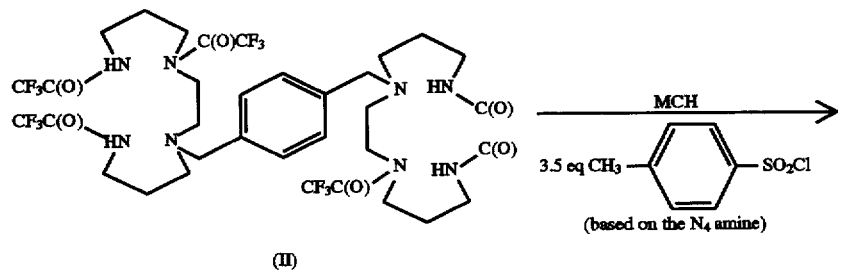

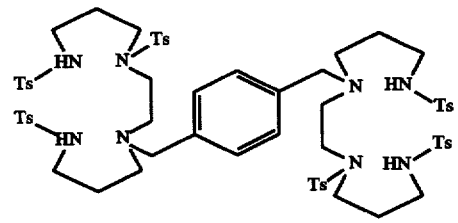

where M is an alkali metal.

STEP 2

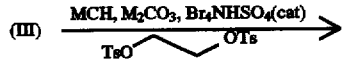

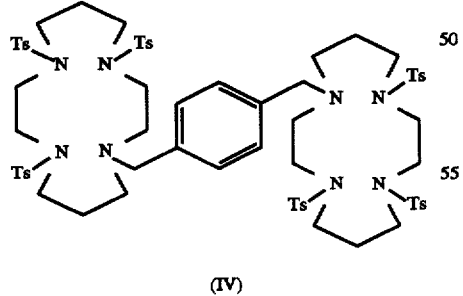

where M is as defined above.

STEP 3

-continued
STEP 3

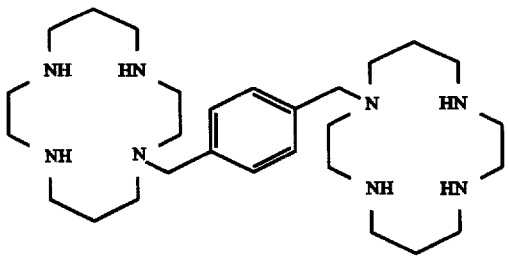

With respect to the individual steps, the first part of step 1 concerns the reaction of N,N'-bis(3-aminopropyl) ethylenediamine with 3 equivalents of ethyl trifluoroacetate to yield the tris-trifluoroacetyl protected acyclic compound of formula I. The selective trisfunctionalization reaction is carried out in the presence of a solvent such as tetrahydrofuran at a temperature of from 10° C. to 35° C. for a period of between 2 and 6 hours.

The second part of Step 1 involves subjecting the compound prepared in the first part, i.e., the acyclic compound of formula I, to dimerization by reacting it with 0.5 equivalents of α,α'-dibromoxylene (as a cyclic ethereal solution, e.g., a tetrahydrofuran solution) in the presence of diisopropylethylamine to obtain the 1,4-phenylenebis-methylene bridged acyclic dimer of formula II. The dimerization is carried out at a temperature of from 15° C. to 70° C. for a period of between 2 and 16 hours.

The third part of Step 1 involves the hydrolysis of the trifluoroacetyl groups of the compound prepared in the second part, i.e., the acyclic dimer of formula II, and the subsequent tosylation of the intermediate to obtain the 1,4-phenylenebis-methylene bridged hexatosyl acyclic precursor of formula III. The hydrolysis is carried out by treating the acyclic dimer of formula II with 6.5 equivalents of an aqueous solution of an alkali metal hydroxide such as sodium hydroxide at a temperature of from 50° C. to 70° C. for a period of between 1.5 and 3 hours. The tosylation is carried out by reacting the intermediate with 3.5 equivalents of p-toluenesulfonylchloride in the presence of a cyclic ether such as tetrahydrofuran at a temperature of from 15° C. to 65° C. for a period of between 4 and 8 hours.

Step 2 involves the cyclization of the compound prepared in the third part of Step 1, i.e., the bridged hexatosyl acyclic precursor of formula III, by reacting it with 3 equivalents of ethyleneglycol ditosylate in the presence of a mixture of an alkali metal hydroxide such as sodium hydroxide (in bead form) and an alkali metal carbonate such as potassium carbonate (in anhydrous form) and a catalytic amount of t-butylammonium sulfate to obtain the hexatosyl cyclam dimer of formula IV. The cyclization is carried out in the presence of dimethylformamide at a temperature of from 75° C. to 125° C. for a period of between 4 and 7 hours.

Alternatively, the bridged hexatosyl acyclic precursor of formula III can be reacted with 3 equivalents of ethyleneglycol ditosylate in the presence of cesium carbonate in dimethylformamide at a temperature of from 75° C. to 125° C. for a period of between 4 and 7 hours to obtain the hexatosyl cyclam dimer of formula IV.

Step 3 concerns the detosylation of the compound prepared in Step 2, i.e., the hexatosyl cylam dimer of formula IV, by reacting it with a mixture of hydrobromic acid (48% solution) and glacial acetic acid. The product is then basified with an alkali metal hydroxide solution (e.g., a 3N sodium hydroxide solution) to obtain the desired compound of formula V. The detosylation is carried out at reflux temperature for a period of between 30 hours and 3 days. Alternatively, the detosylation may be carried out by reacting the compound prepared in Step 2 with concentrated sulfuric acid or with a mixture of sodium phosphate and freshly prepared sodium amalgam in an argon atmosphere. The detosylation with concentrated sulfuric acid may be carried out at a temperature of from 80° C. to 120° C. for a period of between 2 and 5 hours, whereas the detosylation with a mixture of sodium phosphate and sodium amalgam may be carried out at a temperature of from 80° C. to 120° C. for a period of between 1 and 4 days.

Alternatively, the bridged hexatosyl acyclic precursor of formula III may be prepared by the following three-part reaction scheme:

STEP 1A

Part 1        Part 2

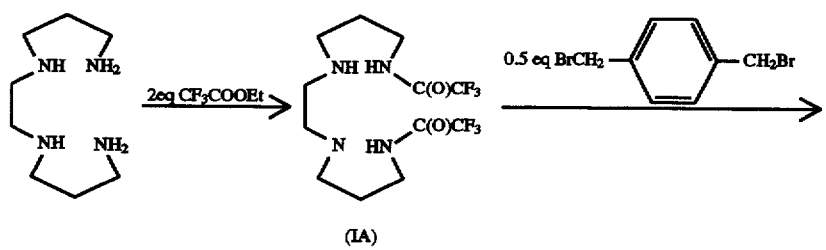

(IA)

Part 3

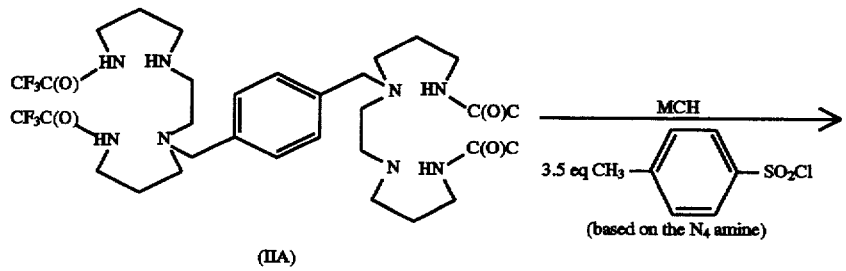

(IIA)

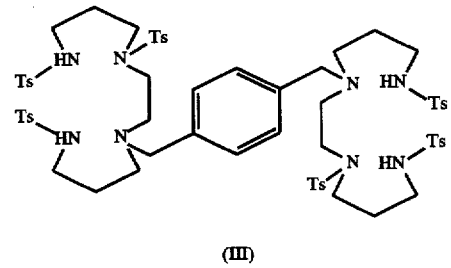

(III)

where M is as defined above.

The first part of Step 1A involves the reaction of N,N'-bis(3-aminopropyl)-ethylenediamine with 2 equivalents of ethyl trifluoroacetate to yield the bisacetamide compound of formula IA. The preparation of the bisacetamide compound is carried out in the presence of a cyclic ether such as tetrahydrofuran at a temperature of from 10° C. to 35° C. for a period of between 1 and 3 hours.

The second part of Step 1A concerns subjecting the compound prepared in the first part, i.e., the bisacetamide compound of formula Ia, to dimerization by reacting it with 0.5 equivalents of α,α'-dibromoxylene (as a cyclic ethereal solution, e.g., a tetrahydrofuran solution) to obtain the 1,4-phenylenebis-methylene bridged acyclic dimer of formula IIA. The dimerization is carried out at a temperature of from 10° C. to 35° C. for a period of between 2 and 6 hours.

The third part of Step 1A involves the hydrolysis of the trifluoroacetyl groups of the compound prepared in the second part, i.e., the acyclic dimer of formula IIA, and the susequent tosylation of the intermediate in essentially the manner described above in the third part of Step 1 above.

The desired compound, i.e., the 1,1'-[1,4-phenylenebis-(methylene)]-bis-1,4,8,11-tetraazacyclotetradecane, may then be obtained by employing the procedures described above in Steps 2 and 3.

As alluded to above, the acyclic tetraamine compound employed as the starting material in the first part of Step 1 or Step 1A is known and commercially available.

Although the product of each reaction described above in the three parts of Step 1 or Step 1A and the product of the reaction described above in Step 2 may, if desired, be purified by conventional techniques such as recrystallization (if a solid), the crude product of one reaction is advantageously employed in the following reaction without purification.

It should be understood that although the instant process is directed to the preparation of the highly potent anti-HIV cyclam dimer 1,1'-[1,4-phenylenebis-(methylene)]-bis-1,4,8,11-tetraazacyclotetradecane in free base form, said compound can be readily converted to pharmaceutically acceptable acid addition salt forms, if desired, in conventional manner. For example, the free base can be reacted with hydrobromic acid to obtain the cyclam dimer in octahydrobromide dihydrate form. Similarly, the addition of saturated hydrochloric acid to the free base yields the cyclam dimer in octahydrochloride dihydrate form.

The tris-trifluoroacetyl compound of formula I, the di-trifluoroacetyl compound of formula 1A and the bridged hexatosyl acyclic precursor of formula III are novel compounds and, as such, also form a part of this invention.

The following examples are for purposes of illustration only and are not intended to limit in any way the scope of the instant invention.

EXAMPLE 1 a) Preparation of the 1,4-phenylenebis-methylene bridged hexatosyl acylic precursor of formula III.

To a 4-necked, round-bottom flask, equipped with a mechanical stirrer, heating mantle, internal thermometer and addition funnel, is added 43.5 g (0.25 mol) of N,N'-bis(3-aminopropyl)ethylenediamine and 250 ml of tetrahydrofuran. To the resultant solution is added, over a period of 30 minutes with external cooling to maintain the temperature at 20° C., 113.6 g (0.8 mol) of ethyl trifluoroacetate. The reaction mixture is then stirred at room temperature for 4 hours, after which time 52.25 ml. (0.3 mol) of diisopropylethylamine is added. The resultant reaction mixture is warmed to 60° C. and, over a period of 2 hours, is added a solution of 33.0 g (0.125 mol) of α,α'-dibromoxylene in 500 ml. of tetrahydrofuran. The reaction mixture is then maintained at a temperature of 60° C., with stirring, for an additional 2 hours after which time a solution of 62.0 g. (1.55 mol) of sodium hydroxide in 250 ml. of water is added. The resultant mixture is then stirred vigorously for 2 hours, while the temperature is maintained at 60° C. A solution of 152.5 g. (0.8 mol) of p-toluenesulfonyl-chloride in 250 ml. of tetrahydrofuran is then added, over a period of 30 minutes, while the temperature is maintained at between 20° C. and 30° C. The reaction is then allowed to proceed for another hour at room temperature. To the reaction mixture is then added 1 liter of isopropyl acetate, the layers are separated and the organic layer is concentrated to dryness under vacuum to yield the desired compound as a foamy material.

b) Preparation of the hexatosyl cyclam dimer of formula IV.

To a 4-necked, round-bottom flask, equipped with a mechanical stirrer, heating mantle, internal thermometer and addition funnel, is added 114.6 g. (0.10 mol) of the compound prepared in a) above and 2.5 liters of dimethylformamide. After the system is degassed, 22.4 g. (0.56 mol) of NaOH beads, 27.6 g (0.2 mol) of anhydrous potassium carbonate and 5.43 g. (0.016 mol) of t-butylammonium sulfate are added to the solution, and the resultant mixture is heated to 100° C. and maintained at this temperature for 2.5 hours. A solution of 111.0 g (0.3 mol) of ethyleneglycol ditosylate in 1 liter of dimethylformamide is then added, over a period of 2 hours, while the temperature is maintained at 100° C. After cooling the reaction mixture to room temperature, it is poured into 4 liters of water with stirring. The suspension is then filtered and the filter cake is washed with 1 liter of water. The filter cake is then thoroughly mixed with 1 liter of water and 2 liters of ethyl acetate. The solvent is then removed from the ethyl acetate solution and the residue is re-dissolved in 500 ml. of warm acetonitrile. The precipitate that forms on standing is collected by filtration and then dried to yield the desired compound as a white solid.

c) Preparation of 1,1'-[1,4-phenylenebis-(methylene)]-bis-1,4,8,11-tetraazacyclotetradecane.

In a 4-necked, round-bottom flask, equipped with a mechanical stirrer, heating mantle, internal thermometer and addition funnel, is added 26.7 g. (0.02 mol) of the compound prepared in b) above, 300 ml. of 48% hydrobromic acid and 1 liter of glacial acetic acid. The resultant mixture is then heated to reflux and maintained at reflux temperature, with stirring, for 42 hours. The reaction mixture is then cooled to between 22° C. and 23° C. over a period of 4 hours, after which time it is stirred for an additional 12 hours. The solids are then collected using suction filtration and added to 400 ml. of deionized water. The resultant solution is then stirred for 25 to 30 minutes at a temperature between 22° C. and 23° C. and filtered using suction filtration. After washing the filter pad with a small amount of deionized water, the solution is cooled to between 10° C. and 15° C. 250 g. of a 50% aqueous solution of sodium hydroxide is then added, over a period of 30 minutes, while the temperature is maintained at between 5° C. and 15° C. The resultant suspension is stirred for 10 to 15 minutes, while the temperature is maintained at between 10° C. and 15° C. The suspension is then warmed to between 22° C. and 23° C. and to the warmed suspension is added 1.5 liters of dichloromethane. The mixture is then stirred for 30 minutes, the layers are separated and the organic layer is slurried with 125 g. of sodium sulfate for 1 hour. The solution is then filtered using suction filtration, and the filtrate is concentrated under reduced pressure (40°–45° C. bath temperature, 70–75 mm Hg) until approximately 1.25 liters of solvent is collected. To the slurry is then added 1.25 liters of acetone, and the filtrate is concentrated under reduced pressure (40°–45° C. bath temperature, 70–75 mm Hg) until approximately 1.25 liters of solvent is collected. The slurry is then cooled to between 22° C. and 23° C. and the solids are collected using suction filtration. The solids are then washed with three 50 ml. portions of acetone and dried in a vacuum oven to obtain the desired compound as a white solid.

EXAMPLE 2

The following is an alternate procedure for the preparation of the 1,4-phenylenebis-methylene bridged hexatosyl acyclic precursor of formula III.

To a 3-necked, round-bottomed flask, equipped with a mechanical stirrer, heating mantle, internal thermometer and addition funnel, is added 3.48 g. (20 mmol) of N,N'-bis-(3-aminopropyl)ethylenediamine and 20 ml. of tetrahydrofuran. To the resultant solution is added, over a period of 20 minutes with external cooling to maintain the temperature at 20° C., 5.2 ml. (42 mmol) of ethyl trifluoroacetate. The reaction mixture is then stirred at room temperature for 1 hour, after which time a solution of 2.64 g. (10 mmol) of α,α'-dibromoxylene in 20 ml. of tetrahydrofuran is added. The resultant reaction mixture is then stirred at room temperature for 4 hours. A solution of 4.8 g. (120 mmol) of sodium hydroxide in 20 ml. of water is then added and the resultant mixture is warmed to 60° C. and maintained at this temperature, with vigorous stirring, for 2 hours. Over a period of 20 minutes, 13.9 g. (73 mmol) of p-toluenesulfonylchloride is then added portionwise, while the temperature is maintained at 20° C. The reaction is then allowed to proceed for another hour at room temperature. To the reaction mixture is then added 100 ml. of isopropyl acetate, the layers are separated and the organic layer is washed with saturated sodium bicarbonate aqueous solution. The solution is then condensed to 40 ml., cooled to 4° C. and kept at that temperature overnight. The resultant suspension is filtered and the solid is washed with 10 ml. of isopropyl acetate. The solvents are then removed from the filtrate to yield the desired compound as a brown gel.

What is claimed is:

1. The tris-trifluoroacetylated compound having the formula

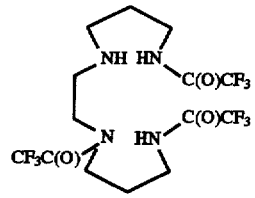

2. The di-trifluoroacetylated compound having the formula

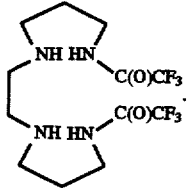

3. The bridged hexatosyl acyclic compound having the formula

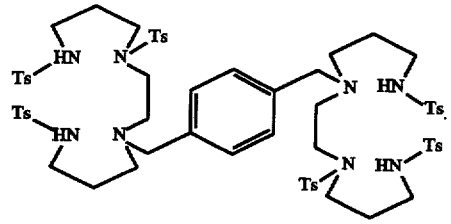

* * * * *